US008420861B2

(12) United States Patent
Ishmael

(10) Patent No.: US 8,420,861 B2
(45) Date of Patent: Apr. 16, 2013

(54) ANTI-TUMOR COMPOUNDS DERIVED FROM 1,4,5,8-TETRACHLOROANTHRAQUINONE

(76) Inventor: D. Richard Ishmael, Oklahoma City, OK (US)

( * ) Notice: Subject to any disclaimer, the term of this patent is extended or adjusted under 35 U.S.C. 154(b) by 0 days.

(21) Appl. No.: 12/253,065

(22) Filed: Oct. 16, 2008

(65) Prior Publication Data

US 2009/0156807 A1    Jun. 18, 2009

Related U.S. Application Data

(60) Provisional application No. 60/980,216, filed on Oct. 16, 2007.

(51) Int. Cl.
*C07C 211/54* (2006.01)
(52) U.S. Cl.
USPC .......................................................... 564/306
(58) Field of Classification Search .................... 564/306
See application file for complete search history.

(56) References Cited

U.S. PATENT DOCUMENTS

| | | | | |
|---|---|---|---|---|
| 2,611,772 | A | * | 9/1952 | Allen et al. .................. 552/255 |
| 2,727,045 | A | | 12/1955 | McSheehy |
| 3,646,072 | A | | 2/1972 | Shaw |
| 4,197,249 | A | | 4/1980 | Murdock et al. |
| 4,278,689 | A | | 7/1981 | Murdock et al. |
| 4,310,666 | A | | 1/1982 | Zee-Cheng et al. |
| 4,446,047 | A | | 5/1984 | Thompson |
| 4,455,253 | A | | 6/1984 | Thompson |
| 4,526,989 | A | | 7/1985 | Murdock et al. |
| 4,585,574 | A | | 4/1986 | Blunck et al. |
| 5,342,974 | A | | 8/1994 | Ohyama et al. |
| 6,465,522 | B1 | | 10/2002 | Potter et al. |
| 6,811,575 | B2 | | 11/2004 | Ho et al. |

OTHER PUBLICATIONS

Huang, et al. Helvetica Chimica Acta. vol. 87, 2004, pp. 999-1006.*
Agbandje, et al., "Anthracene-9,10-diones as potential anticancer agents. Synthesis, DNA-binding, and biological studies on a series of 2,6-disubstituted derivatives", "Journal of Medicinal Chemistry", 1992, pp. 1418-1429, vol. 35, No. 8, Publisher: ACS Publications, Published in: US.
Greenhalgh, et al., "The Reaction of Leucoquinizarins with Alkylenediamines", "Journal of Medicinal Chemistry", 1968, pp. 1284-1288, Publisher: J. Chem. Soc., Published in: US.
Islam, et al., "Comparative Computer Graphics and Solution Studies of the DNA Interaction of Substituted Anthraquinones Based on Doxorub", "Journal of Medicinal Chemistry ", 1985, pp. 857-864, vol. 28, No. 7, Publisher: American Chemical Society, Published in: US.
Murdock, et al., "Antitumor agents. 1. 1,4-Bi[(aminoalkyl)amino]-9,10-anthracenediones", "Journal of Medicinal Chemistry", 1979, pp. 1024-1030, vol. 22, No. 9, Publisher: ACS Publications, Published in: US.
Zee-Cheng, et al., "Antineoplastic agents. Structure-activity relationship study of bis(substituted aminoalkylamino) anthraquionones", "Journal of Medicinal Chemistry", 1978, pp. 291-294, vol. 21, No. 3, Publisher: ACS Publications, Published in: US.
Mosmann, Rapid Colorimetric Assay for Cellular Growth and Survival: Application to Proliferation and Cytoxicity Assays, 1983, pp. 55-63, vol. 65, Publisher: Journal of Immunological Methods, Published in: US.
Nordquist, et al., The Tissue Culture and Morphology of Human Breast Tumor Cell Line BOT-2, Nov. 1975, pp. 3100-3105, vol. 35, Publisher: Cancer Research, Published in: US.

* cited by examiner

*Primary Examiner* — Shawquia Young
(74) *Attorney, Agent, or Firm* — Fellers, Snider, Blankenship, Bailey & Tippens, P.C.

(57) ABSTRACT

Compounds for utilization as anti-tumor agents against cancer and certain inflammatory and arthritic conditions designed with multiple active sites to cause inhibition and cell death synthesized from the starting compound 1,4,5,8-tetrachloroanthraquinone. Included are anti-tumor compounds of the class 1,4,5,8-tetrakis-alkylaminoalkyl, 1,4,5,8-tetrakis-hydroxyalkylaminoalkyl, 1,4,5,8-tetrakis-chloroethylamino, 1,2-bischloroethylamino-1,4,5,8-tetrakis-aminoethylamino derivatives of Anthraquinone. Also includes mixtures of groupings such as 1-aminoalkylamino-4,5,8-tris-(1,2-dimethyl)aminoalkylamino anthraquinone, 1,2-dichloroethyl 1-aminoalkyl amino-4,5,8-tris-aminoethylamino anthraquinone, bis-1,4aminoalkylamino bis-5,8-alkylaminoanthraquinone, 1,4-bis-chloroalkylamino-5,8-bisaminoalkylamino anthraquinone and others.

10 Claims, No Drawings

ANTI-TUMOR COMPOUNDS DERIVED FROM 1,4,5,8-TETRACHLOROANTHRAQUINONE

This application claims the benefit of U.S. Provisional Patent Application Ser. No. 60/980,216, filed on Oct. 16, 2007, the disclosure of which is incorporated herein by reference as if fully set out at this point.

FIELD OF THE INVENTION

This disclosure relates to cancer drugs in general and, more specifically, to anti-tumor compounds derived from 1,4,5,8-tetrachloroanthraquinone

BACKGROUND

It is known that certain 1,4 bishydroxyethylaminoethylamino and 1,4,aminoethylaminoanthraquinones have anti-cancer activity. One of these compounds bis1,4 hydroxyethylaminoethylamino 5,8-dihydroxyanthraquinone dihydrochloride is on the market for treatment of certain cancers including acute leukemia, lymphoma, breast cancer and prostate cancer. It is known under the generic name as mitoxantrone and under the marketing name of Novantrone®. This compound and 1.4 his aminoalkylamino 5,8-dihydroxyanthraquinone compounds were patented by Murdock et al. in 1981. The impetus for synthesizing these compounds came from structure function relationships of the drug hydroxydaunomycin, daunorubicin, adriamycin® approved for the treatment of cancer and leukemia. This drug had a structure similar to the compounds produced by Murdock et al. and also by Zee-Cheng and Cheng. The daunorubicin was one of the most active drugs then known but had a draw back because it has been linked to cause heart failure.

Subsequent studies have revealed that mitoxantrone usually has less activity than daunorubicin although they both have generally equal survival rates. The drug has also shown activity in the treatment of multiple sclerosis and is approved for the treatment of multiple sclerosis. It also showed activity in the treatment of adjuvant arthritis in a rat model. Mitoxantrone although utilized, has not been a popular anticancer drug in humans. A recent patent revealed that alkylating groups could be placed at the 1,4 position in the anthraquinone molecule resulting in compounds with good activity with reduced drug resistance. Anthraquinone compounds with groupings at the 2,6 position has activity to inhibit telomerase activity. Anti telomerase activity is a known target against cancer. Substitutes at the 1,5 and 1,8- have shown anticancer activity. A patent issued to Potter et al (U.S. Pat. No. 6,465,522) includes a novel family of anticancer drugs comprising an anthraquinone group linked to an alkylating agent, the agents having potent anticancer activity and displaying potent activity against drug-resistant tumors. The clinical response to anticancer agents in cancer chemotherapy is ultimately limited by the emergence of drug resistant cells.

The anthraquinone group of the molecules is found in a number of molecules having anticancer activity, for example adriamycin and mitoxantrone (Islam et al., 1985, J. Med. Chem., 28: 857). In adriamycin the anthraquinone group is present as part of an anthracycline structure. Typically, drugs containing the anthraquinone group show cross-resistance with adriamycin, i.e. anthraquinone analogues usually show poor activity against adriamycin resistant tumors. Thus, a need exists for compounds that have greater therapeutic index. Typically anti-cancer bis-aminoalkylamino or bis-hydroxyalkylaminoalkylamino compounds are synthesized from 1,4,5,8-tetrahydroxyanthraquinone usually as the leuco form which is more reactive. The hydroxyl groups of the M-S carbon undergo reaction and typically the other two hydroxyl groups do not. Higher temperatures or longer reaction times may give a tris derivative but not a tetrakis derivative. Also higher temperatures of the reaction gives a cyclical derivative that is considerably less active. Chlorine groups can be replaced by the amino chlorine substitution. In the anthraquinone series, chlorine groups can be replaced in the 1,4,5 or 8 positions utilizing alkyli and copper salts. Benzyl alcohol improves the substitution by increasing the effectiveness of the catalytic effect of the copper salt.

A review of the literature revealed several patents that showed that all four chlorine groups could be replaced. Kim Sang Ho, Yu-Min Chen, U.S. Pat. No. 6,811,575 Nov. 2, 2004, described a method for marking hydrocarbons with anthraquinones. These compounds are tetra derivatives of 1,4,5,8-tetrachloroanthraquinone. Also Tsukasa Ohyama; Shizuo Kuroda; Keisuke Takunia; Hiroshi Aig, U.S. Pat. No. 5,342,974 1994 described derivatives of tetra halogenated anthraquinone and their use as near infrared rays absorbing optical filters. Finally David J. Thompson U.S. Pat. No. 4,446,047 1984 and U.S. Pat. No. 4,455,253 1984 described pleochroic anthraquinone dyes synthesized from 1,4,5,8-tetrachloroanthraquinone.

SUMMARY OF THE INVENTION

The present invention provides new compounds for the utilization against cancer and certain inflammatory and arthritic conditions. Antitumor agents are designed with multiple active sites to cause inhibition and cell death of cancer. Utilizing known intercalating sites of inhibition of topoisomerase II enzymes, DNA cross-linking, enzyme inhibition and free radical formation, compounds were designed and synthesized from the starting compound 1,4,5,8-tetrachloro anthraquinone.

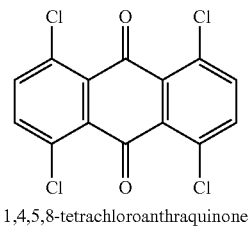 [SMILES: O=C1c2c(Cl)ccc(Cl)c2C(=O)c2c(Cl)ccc(Cl)c21]

1,4,5,8-tetrachloroanthraquinone

The present invention includes anti-tumor compounds of the class 1,4,5,8-tetrakis-alkylaminoalkyl, 1,4,5,8-tetrakis-hydroxyalkylaminoalkyl, 1,4,5,8-tetrakis-chloroethylamino, 1,2-bischloroethylamino-1,4,5,8-tetrakis-aminoethylamino derivatives of Anthraquinone. The invention also includes mixtures of groupings such as 1-aminoalkylamino-4,5,8-tris-(1,2-dimethyl)aminoalkylamino anthraquinone or 1,2- dichloroethyl 1-aminoalkyl amino-4,5,8-tris-aminoethylamino anthraquinone. Bis-1,4-aminoalkylamino bis-5,8-alkylaminoanthraquinone and 1,4-bis-chloroalkylamino-5,8-bisaminoalkylamino anthraquinone. Many examples of side groupings are shown in this disclosure but it should be understood that the groupings are not limited to those shown.

Additionally, it has been found that the compounds above enhanced synergistically a variety of other anticancer drugs.

DETAILED DESCRIPTION OF THE INVENTION

Using different side chain reactants, compounds were synthesized for the purpose of anti cancer chemotherapeutic compounds. In one embodiment, the synthesis is 99% 1,4,5,8-tetrachloroanthraquinone with sodium acetate to react with hydrogen chloride produced, cupric chloride in catalytic amounts with benzyl alcohol and an amine in excess such as N,N-dimethylethylenediamine are mixed and heated to 100° to 130° C. for generally 4 to 8 hours under a nitrogen atmosphere.

Primary Amines

A number primary amines can be utilized in primary reactions such as: alkyldiamines, hydroxyalkylamines, halogenalkylamines, aminoalkylnitriles, aminoalkylaminoalkylamines, hydroxyalkylaminoalkylamines, polyamines such as: cadaverine, spermine, and spermidine. Also other chemotherapeutic agents such as mitoguazone (MGBG) can be utilized where primary amino groups are exposed for reaction. This would include adding other agents with amino groups such as amino sugars such as found in adriamycin (hydroxydaunomycin, doxorubicin), daunomycin, epirubicin and similar anticancer compounds through linkages such as 1,2 dibromoethane. Further reactions of the primary amines would include metal binding to add platinum or other heavy metal groups to give molecules with further active groups for anticancer effect. Because of their binding to heavy metals compounds with radioactive uranium, radium, technetium, samarium ($^{153}$Sm), $^{131}$I, anticancer compounds with the ability to attack the cancer cell in multiple ways and therefore have the potential to have greater effect with a single dose.

Secondary Amines

Secondary amines can be dialkylamines or diaralkylamines such as dimethylamine, diethylamine, dipropylamine, methylethylamine, ethylpropylamine, dibensylamine, diphenethylamine, 'etc. Also, 'the secondary amine can be compounds such as ethylenimine, pyrrolidine, piperidine, morpholine, thianiorpholine, tetrahydroquinoline, 1-alkyl substituted piperazines. The ethylenimines used in the preparation of the products' of the present invention can be compounds such as 2-methylethylenimine, 2,2-di-methylethylenimine, 2-ethylethylenimine, 2-propylethylenimine, 2-hexylethylenimine, 2,2-di-ethylethylenimine, ethylenimine itself. These ethylenimine intermediates may be prepared by ring closure with an alkali metal hydroxide of the corresponding 2-haloethylamine or of the sulfuric ester of the corresponding 2-hydroxyethyl-amine. The reaction to prepare the compounds of the present invention is preferably carried out in an organic solvent such as benzene, ether, and dioxane. It is' also necessary to have present an acid acceptor which may be a tertiary amine such as triethylamine, N-ethylmorpholine or pyridine. The reaction can also be carried out in water or in a substantially aqueous solution in which reaction acid acceptors are also required to neutralize the hydrohalide acid formed. Under these circumstances, the acid acceptor may be an alkaline substance such as alkali metal carbonate or bicarbonate. Isolation of the product from the organic solvent may be accomplished by filtration of the tertiary amine hydrochloride salt and crystallization from the organic solvent or by evaporation of the organic solvent. When the compounds are prepared in an aqueous medium some of the members may be isolated by filtration. Others may be extracted from the aqueous solution by the use of organic solvents. The procedure will vary with individual members. The reaction is generally carried out at a temperature within the range of 0° C. to about 60° C. At this temperature range the reaction is usually complete within a period of thirty minutes to about five to six hours.

Examples of Active Structures

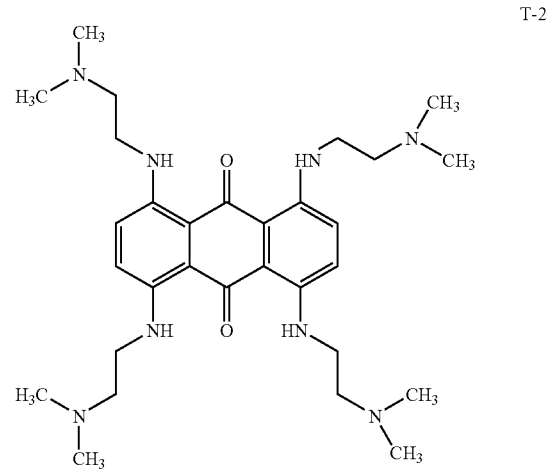

T-2

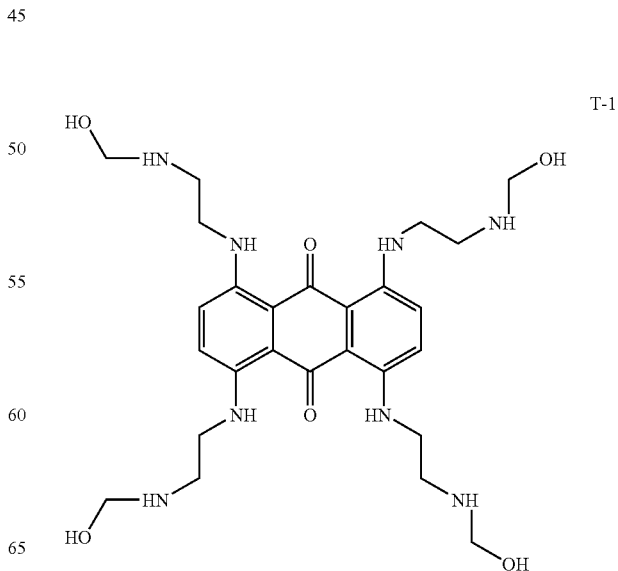

T-1

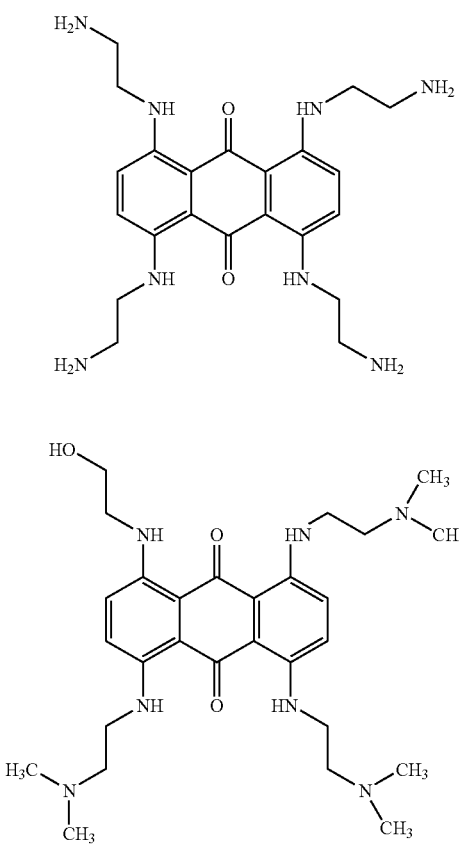

T-4

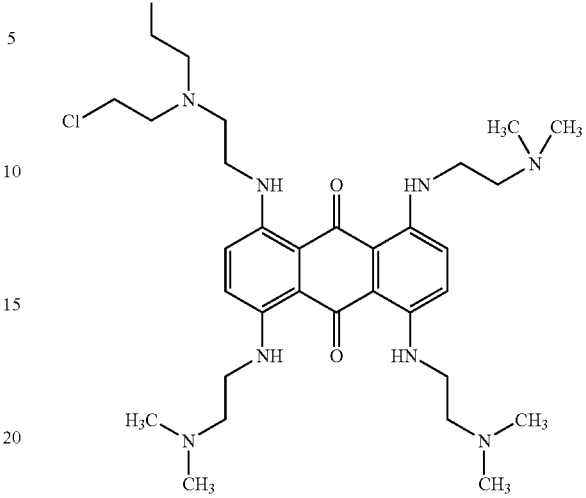

T-2,2,23

T-2,2,2,10

The synthesized compounds tested were compared to mitoxantrone (Novantrone®) when tested in a tissue culture system using the BOT-2 breast cancer cell line. The MTT assay was used to determine levels of 100% and 50% cell kill. In addition to activity against cancer mitoxantrone has been used to treat certain forms of multiple sclerosis and is approved by the FDA to treat both cancer and multiple sclerosis. Mitoxantrone also has significant immune modulatory effects and could be used to treat severe forms of collagen vascular disorders. The compounds described in the present disclosure would be expected to have similar activities at a greater therapeutic efficacy.

Table of Side Chains

| Designation | Side chain 1, 4 | Side chain 5, 8 | Activity |
| --- | --- | --- | --- |
| T-1 | aminoethylaminoethanol | aminoethylaminoethanol | 5 |
| T-2 | N,N'dimethylethylene diamine | N,N'dimethylethylene diamine | 5 |
| T-3 | ethanolamine | ethanolamine | 1 |
| T-4 | ethylenediamine | ethylenediamine | 5 |
| T-5 | diaminopropane | diaminopropane | |
| T-6 | diaminobutane | diaminobutane | |
| T-7 | dihydroxyethylamine | dihydroxyethylamine | |
| T-8 | chloroethylamino | chloroethylamino | |
| T-9 | Bischloroethylaminoethyl amino | Bischloroethylaminoethyl amino | |
| T-10 | ethylenimine | ethylenimine | |
| T-11 | 2-(diethylamino)ethylamine | 2-(diethylamino)ethylamine | |
| T-12 | 2-(Diethylamino)ethyl aminoethyl | | |
| T-13 | 2-morpholinoethylamino | 2-morpholinoethylamino | |
| T-14 | 2-(1-pyrrolidinyl)-ethyl]amino | 2-(1-pyrrolidinyl)-ethyl]amino | |
| T-15 | 2.(1-piperazinyl)ethylamino | | |
| T-16 | cyano morpholinoethylamino | | |
| T-1,1-2,2 | aminoethylaminoethanol | dimethylethylenediamine | 4 |
| T-1,1-3,3 | aminoethylaminoethanol | ethanolamine | |
| T-1,1-4,4 | aminoethylaminoethanol | ethylenediamine | |
| T-1,1-5,5 | aminoethylaminoethanol | diaminopropane | |
| T-1,1-6,6 | aminoethylaminoethanol | diaminobutane | |
| T-1,1-7,7 | aminoethylaminoethanol | bishydroxyethylamine | |
| T-1,1,1.8 | aminoethylaminoethanol | chloroethylamino | |
| T-1,1,1,8-9 | aminoethylaminoethanol | Bischloroethylaminoethyl amino | |
| T-2,2,2,4 | N,N'dimethylethylene diamine | ethylenediamine | |

| | Table of Side Chains | | |
|---|---|---|---|
| T-2,2,4,4 | N,N'dimethylethylene diamine | ethylenediamine | |
| T-2,4,4,4 | N,N'dimethylethylene diamine | ethylenediamine | |
| T-2,2,2,3 | N,N'dimethylethylene diamine | ethanolamine | 5 |
| T-2,2,3,3 | N,N'dimethylethylene diamine | ethanolamine | 5 |
| T-2,3,3,3 | N,N'dimethylethylene diamine | ethanolamine | |
| T-2,2,2,10 | N,N'dimethylethylene diamine | ethylenimine | |
| T-3,3,3,4 | ethanolamine | ethylenediamine | 4 |
| T-3,3,4,4 | ethanolamine | ethylenediamine | 5 |
| T-3,4,4,4 | ethanolamine | ethylenediamine | 5 |
| T-4,4,4,8 | ethylenediamine | chloroethylamine | |
| T-4,4,8,8 | ethylenediamine | chloroethylamine | |
| T-4,8,8,8 | ethylenediamine | chloroethylamine | |
| T-2,8,8,8 | N,N'dimethylethylene | chloroethylamino | |
| T-2,2,8,8 | N,N'dimethylethylene diamine | chloroethylamino | |

| designation | 1, 4, 5 side chains | 8 side chain | activity |
|---|---|---|---|
| T-1,1,1,2 | aminoethylaminoethanol | N,N'dimethylethylene diamine | |
| T-2,2,2,1 | N,N'dimethylethylene diamine | aminoethylaminoethanol | 5 |
| T-2,2,2,11 | N,N'dimethylethylene diamine | 2-(diethylamino)ethylamine | |
| T-2,2,11,11 | N,N'dimethylethylene diamine | 2-(diethylamino)ethylamine | |
| T-2,11,11,11 | N,N'dimethylethylene diamine | 2-(diethylamino)ethylamine | |
| T-2,2,2,12 | N,N'dimethylethylene diamine | 2-(Diethylamino)ethyl amino | |
| T-2,2,12,12 | N,N'dimethylethylene diamine | 2-(Diethylamino)ethyl amino | |
| T-2,12,12,12 | N,N'dimethylethylene diamine | 2-(Diethylamino)ethyl amino | |
| T-2,2,2,13 | N,N'dimethylethylene diamine | 2-morpholinoethylamino | |
| T-2,2,2,14 | N,N'dimethylethylene diamine | 2-(1-pyrrolidinyl)-ethyl]amino | |
| T-2,2,14,14 | N,N'dimethylethylene diamine | 2-(1-pyrrolidinyl)-ethyl]amino | |
| T-2,2,2,15 | N,N'dimethylethylene diamine | 2.(1-piperazinyl)ethylamino | |
| T-2,2,15,15 | N,N'dimethylethylene diamine | 2.(1-piperazinyl)ethylamino | |
| T-4,4,4,1 | ethylenediamine | aminoethylaminoethanol | |
| T-4,4,4,5 | ethylenediamine | diaminopropane | |
| T-4,4,4,6 | ethylenediamine | diaminobutane | |
| T-4,4,4,7 | ethylenediamine | dihydroxyethylamine | |
| T-4,4,4,8 | ethylenediamine | chloroethylamino | |

Further examples of combinations of the above amines using the sequences provided.

SYNTHESIS

Example 1

Synthesis of 1,4,5,8-tetra-kis-aminoethylaminoanthraquinone

Seven grams (7 gm) of 1,4,5,8-tetrachloroanthraquinone, 12 gms of sodium acetate, 1 g of cupric sulfate, 3 ml of benzyl alcohol and 60 ml of ethylenediamine were mixed by stirring and heated under $N_2$ to 125° C. The heating and stirring were continued with reflux for 6 hrs. The flask was cooled to 60° and mixed with 400 ml of water with vigorous stirring. The pH of the mixture was 9.4. The mixture was allowed to sit in the cold for 1 hour. The flask was decanted and the precipitate was washed with cold water. Following this, 200 ml of 3 N hydrochloric acid/water was added and the mixture stirred for 2 hours. The solution was filtered and the solute collected and ammonia hydroxide solution was added slowly with stirring until a precipitate formed. The ppt was collected either by filtration or centrifugation. The solid was washed with tetrahydrofuran and dried under vacuum and phosphorous pentoxide.

Example 2

Synthesis of 1,4,5,8-tetra-kis-hydroxyethylaminoethylaminoanthraquinone

First, 7 gm of 1,4,5,8-tetrachloroanthraquinone, 12 gms of sodium acetate, 1 g of cupric sulfate, 3 ml of benzyl alcohol and 70 ml of aminoethylaminoethanol were mixed by stirring and heated under $N_2$ to 125° C. The heating and stirring were continued with reflux for 6 hrs. The flask was cooled to 60° and mixed with 400 ml of water with vigorous stirring. The pH of the mixture was 9.4. The mixture was allowed to sit in the cold for 1 hour. The flask was decanted and the precipitate was washed with cold water. Following this, 200 ml of 3 N hydrochloric acid/water was added and the mixture stirred for 2 hours. The solution was filtered and the solute collected and ammonia hydroxide or sodium hydroxide 15% solution was added slowly with stirring until a precipitate formed. The ppt was collected either by filtration or centrifugation. The solid was washed with tetrahydrofuran and dried under vacuum and phosphorous pentoxide.

Example 3

Synthesis of 1,4,Bis-N,N-dimethylaminoethylamino-5,8,bis-(2-chloroethylamino)anthraquinone First, 7 gm of 1,4,5,8-tetrachloroanthraquinone, 12 gms of sodium acetate, 1 g of cupric sulfate, 3 ml of benzyl alcohol and 10 ml of chloroethylamine, 40 ml of N,N-dimethylethylenediamine were mixed by stirring and heated under $N_2$ to 125° C. The heating and stirring were continued with reflux for 6 hrs. The flask was cooled to 60° and mixed with 400 ml of water with vigorous stirring. The pH of the mixture was 9.4. The mixture was allowed to sit in the cold for 1 hour. The flask was decanted and the precipitate was washed with cold water. Following this, 200 ml of 3 N hydrochloric acid/water was added and the mixture stirred for 2 hours. The solution was filtered and the solute collected and ammonia hydroxide or sodium hydroxide 15% solution was added slowly with stirring until a precipitate formed. The ppt was collected either by filtration or centrifugation.

Example 4

Synthesis of 1,4,5,8-tetra-kis-N,N-dimethylaminoethylamino anthraquinone

Seven grams (7 gm) of 1,4,5,8-tetrachloroanthraquinone, 12 gms of sodium acetate, 1 g of cupric sulfate, 3 ml of benzyl alcohol and 70 ml of N,N-dimethylethylenediamine were mixed by stirring and heated under $N_2$ to 125° C. The heating and stirring were continued with reflux for 8 hrs. The flask was cooled to 60° and mixed with 400 ml of water with vigorous stirring. The pH of the mixture was 9.4. The mixture was allowed to sit in the cold for 1 hour. The flask was decanted and the precipitate was washed with cold water. Then, 200 ml of 15% acetic acid/water was added and the mixture stirred for 2 hours. The solution was filtered and the solute collected and ammonia hydroxide or sodium hydroxide 15% solution was added slowly with stirring until a precipitate formed. The ppt was collected either by filtration or centrifugation. The ppt was dissolved in acetonitrile with heating and filtered. The solvent was evaporated and the solid dried under $P_2O_5$ in a high vacuum.

This material was used in cytotoxicity assay and material was sent to Midwest Research Institute for analysis of the structure and purity.

Testing of Compounds by the MTT Assay

Testing of compounds in the MTT assay. In a 72 well plate, the BOT-2 human breast cancer cells were allowed to grow for 24 hours. Following this growth time, dilutions of the drug was added. The cells were checked for percentage of cell death at 24 and 48 hours. This checking was done by visual appearance of the cells. Rounded up floating cells or disrupted cells indicating cell death. Cells flattened and attached to the bottom of the tissue culture flask indicated alive and healthy cells. At 144 hours MTT.

Visual inspection assay: BOT-2 cancer cells after treatment with an anthracycline or cytotoxic anthraquinone compounds. The dead cells become rounded, detach and float. The compound is initially dissolved in 0.1 N hydrochloric acid or dilute acetic acid. Serial 1 to 4 dilutions of the compound are made with buffered tissue culture media and pipetted into a wells of a 72 well microtiter plate. Determination is made of 100% cell death at 24, 48 and 144 hours for each well. Controls are always run concurrently. This is recorded as the concentration of the compound to give this 100% kill. Previous work has determined if 100% kill is noted there is never re-growth of the tumor cells. Previous work confirmed that visual observation gave results identical to the standard MTT cytotoxicity assay.

Results:

For the compound in example #1

A solution of 1,4,5,8-Tetrakis-[2-(2-aminoethyl)amino]anthraquinone dihydrochloride (T-4) was made of 10 mg/ml in de-ionized water. This was then diluted to 1 mg/ml. This solution was filtered to sterilize. Seventy micro liters (70 µl) of this was mixed with tissue culture media and added to 70 well plate. Two hundred ten (210) cells per well were previously grown for 24 hrs prior to adding the test drug. The test compounds were added in serial 1 to 3 dilutions. 1,4,5,8-Tetrakis-[2-(2-aminoethyl)amino]anthraquinone (T-4) was tested against mitoxantrone, epirubicin, and bis-1,4-aminoethylamino-5,8-dihydroxyanthraquinone. There was also a control in which no drug was added. There was no cell death in the control wells. The end point for positive cell kill was 100% cell death. The 100% cell kill went out to 5, 1:4 dilutions for 1,4,5,8-Tetrakis-[2-(2-aminoethyl)amino]anthraquinone (T-4).

For the compound in example #2:

A solution of 1,4,5,8-Tetrakis-N,N-dimethylaminoethylaminoanthraquinone dihydrochloride was made of 10 mg/ml in de-ionized water. This was then diluted to 1 mg/ml. This solution was filtered to sterilize. 70 µl of this was mixed with tissue culture media and added to 70 well plate. Two hundred ten (210) cells per well were previously grown for 24 hrs prior to adding the test drug. The test compounds were added in serial 1 to 3 dilutions. The 1,4,5,8-Tetrakis-N,N-dimethylaminoethylaminoanthraquinone was tested against mitoxantrone (bis-1,4-hydroxyethylaminoethylamino-5,8-dihydroxyanthraquinone dihydrochloride), epirubicin, and 1,4-bis-[(aminoethyl)amino]anthraquinone. There was also a control in which no drug was added. There was no cell death in the control wells. The end point for positive cell kill was 100% cell death. The 100% cell kill went out to 4 or 5, 1:4 dilutions for all the drugs except The 1,4,5,8-Tetrakis-[(2-hydroxyethyl)amino]anthraquinone dihydrochloride was inactive which went out only 1 dilutions at 24, 48 and 144 hrs.

Testing tetrakis-1,4,5,8-hydroxyalkylaminoethylaminoanthraquinone dihydrochloride in doublet combinations with other chemotherapy drugs gave a synergistic cell kill (greater than additive). These other drugs included docetaxel, gemcitabine and topotecan. This extent of synergism was not seen with mitoxantrone (bis-1,4-hydroxyethylaminoethylamino-5,8-dihydroxyanthraquinone dihydrochloride.

Testing of active compounds in the rat breast cancer model and various mouse models including the B-16 mouse model.

Summary: Many compounds of the class 1,4,5,8-tetrakis-hydroxyalkylaminoalkylamino and 1,4,5,8-tetrakis-aminoalkylaminoanthraquinones had anti-cancer activity as judged by the cytotoxicity assay. Four of the compounds synthesized and tested were more active than mitoxantrone. These were: 1,4,5,8-Tetrakis-{[2-[(2-hydroxyethyl)aminoethyl]amino}anthraquinone (T-1), 1,4,5,8-Tetrakis-[(2-N,N-dimethylaminoethyl)amino]anthraquinone (T-2)1,4,5,8-Tetrakis-[2-(2-aminoethyl)amino]anthraquinone (T-4), and 1,4,5-Tris-(N,N-dimethylamino),8-(2-chloroethylamino) anthraquinone (T-2,2,2,8), 1,4,5-Tris-(2-N,N-dimethylaminoethyl)amino-8-[(2-bischloroethylamino)-2-ethylamino]anthraquinone (T-2,2,2,8-11). This could have significant impact in cancer therapy in humans.

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention as defined by the appended claims.

What is claimed is:

1. A compound of the formula:

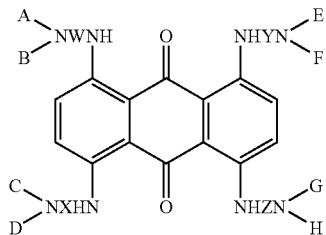

wherein W is an ethyl group; X is an ethyl group; Y is an ethyl group; Z is an ethyl group; and wherein A,B,C,D, E,F,G, and H are all the same and are selected from the group consisting of hydrogen, hydroxyethyl, hydroxymethyl and methyl chains.

2. The compound according to claim 1 wherein A,B,C,D, E,F,G,H are all methyl chains.

3. The compound according to claim 1 wherein A,B,C,D, E,F,G,H are all hydrogen.

4. A compound: 1,4,bis[(2-dimethylaminoethyl)amino]-5,8-bis[(2-aminoethyl)amino] anthraquinone.

5. A compound: 1,4,bis[(2-dimethylaminoethyl)amino]-5,8-bis[(2-hydroxyethyl)amino]amino-anthraquinone.

6. A compound: 1,4,5,8-tetra-kis[2-aminoethyl]amino-anthraquinone.

7. A compound: 1,4,5,8-tetra-kis[2-dimethylaminoethyl] amino-anthraquinone.

8. The compound according to claim 1, wherein the compound is 1,4,5,8-tetra-kis-hydroxyethylaminoethyl amino anthraquinone.

9. A compound: 1,4bis-N,N-dimethylaminoethylamino-5,8,bis-(2-dichloroethylamino) anthraquinone.

10. A compound 1,4,5,8-tetra-kis[2-hydroymethyl aminoethyl]amino anthraquinone.

* * * * *

UNITED STATES PATENT AND TRADEMARK OFFICE
CERTIFICATE OF CORRECTION

PATENT NO. : 8,420,861 B2  
APPLICATION NO. : 12/253065  
DATED : April 16, 2013  
INVENTOR(S) : Ishmael Page 1 of 1

It is certified that error appears in the above-identified patent and that said Letters Patent is hereby corrected as shown below:

In The Claims

COL. 12, LINE 6, Claim 1 the word "hydroxymethyl" is hereby deleted.

Signed and Sealed this
Twenty-seventh Day of January, 2015

Michelle K. Lee
*Deputy Director of the United States Patent and Trademark Office*